United States Patent
Müller et al.

(10) Patent No.: US 6,903,823 B1
(45) Date of Patent: Jun. 7, 2005

(54) METHOD AND DEVICE FOR THE QUANTITATIVE GAS ANALYSIS

(76) Inventors: Holger Müller, Dechant-Wessing-Strasse 1, 45663 Recklinghausen (DE); Udo Schmala, Winnlohstrasse 12, 45663 Recklinghausen (DE)

(*) Notice: Subject to any disclaimer, the term of this patent is extended or adjusted under 35 U.S.C. 154(b) by 281 days.

(21) Appl. No.: 10/088,428

(22) PCT Filed: Sep. 15, 2000

(86) PCT No.: PCT/DE00/03254
§ 371 (c)(1),
(2), (4) Date: Mar. 15, 2002

(87) PCT Pub. No.: WO01/20294
PCT Pub. Date: Mar. 22, 2001

(30) Foreign Application Priority Data

Sep. 15, 1999 (DE) .......................... 199 44 260

(51) Int. Cl.⁷ .............................................. G01N 21/61
(52) U.S. Cl. .......................... 356/437; 356/440; 435/39
(58) Field of Search .................................. 356/437, 440; 435/39

(56) References Cited

U.S. PATENT DOCUMENTS

| | | | |
|---|---|---|---|
| 4,188,126 A | 2/1980 | Boisde et al. | 356/440 |
| 4,220,715 A | 9/1980 | Ahnell | 435/34 |
| 4,889,992 A | 12/1989 | Hoberman | 250/343 |
| 5,232,839 A | 8/1993 | Eden et al. | 435/39 |
| 5,625,189 A * | 4/1997 | McCaul et al. | 250/343 |
| 5,880,850 A * | 3/1999 | McAndrew et al. | 356/437 |
| 6,157,455 A * | 12/2000 | Pinvidic et al. | 356/437 |

FOREIGN PATENT DOCUMENTS

| | | |
|---|---|---|
| DE | 195 18913 C1 | 5/1995 |
| DE | 196 19 673 A1 | 5/1996 |
| DE | 196 50 302 A1 | 12/1996 |
| DE | 197 50 133 A1 | 11/1997 |
| DE | 298 02 972 U1 | 2/1998 |
| DE | 198 21 136 A1 | 5/1998 |
| DE | 198 30 019 A1 | 7/1998 |
| DE | 198 36 215 A1 | 8/1998 |
| EP | 0 905 229 A2 | 8/1998 |
| WO | WO 90/13663 | 11/1989 |
| WO | WO 94/20013 | 9/1994 |
| WO | WO 97/08337 | 3/1997 |

OTHER PUBLICATIONS

English translation of International Preliminary Examination Report of PCT/DE/00/03254.

* cited by examiner

Primary Examiner—Richard A. Rosenberger
(74) Attorney, Agent, or Firm—Young & Basile, P.C.

(57) ABSTRACT

The invention relates to a device and a method for the quantitative gas analysis in which the gas analysis of a sample atmosphere is implemented by means of a sensor device, a diffusion seal being produced between the sample atmosphere contained in a sample system and a measuring chamber and the gas analysis of the sample atmosphere which is diffused into the measuring chamber being implemented with the sensor device, the sensor head (5) being able to be coupled to the measuring adapter (4) and the radiation source (16) and the detector device (17) being fixed to the measuring chamber (9) in a defined orientation and the measuring radiation (24) emitted from the radiation source (16) traversing at least once through the measuring chamber (9) and being detected by the detector device (17) after leaving the measuring chamber (9).

39 Claims, 12 Drawing Sheets

A

METHOD AND DEVICE FOR THE QUANTITATIVE GAS ANALYSIS

BACKGROUND OF THE INVENTION

Figure 1:
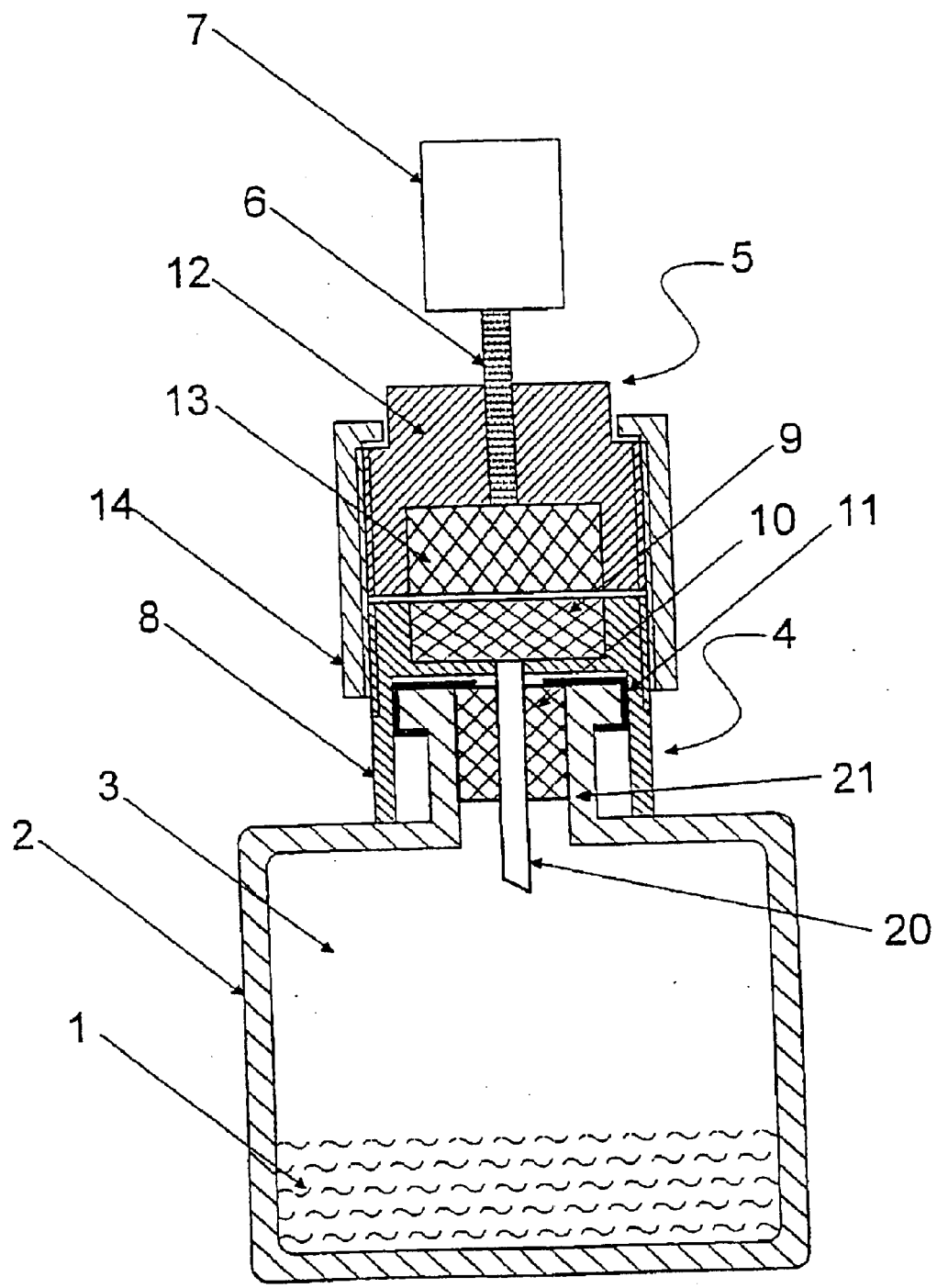

It is known to use carbon dioxide as representative parameter for measuring biological activities. Such measurements of biological activities are used for example for identifying the presence of micro-organisms in a sample, for example blood. Likewise the biological or the chemical oxygen requirement (BOD, COD) can be determined in this manner. A further application example of $CO_2$ measurement is composting of plastic materials in which the plastic materials are treated with micro-organisms and nutrient solution. Monitoring of the progress of the decomposition during composting is implemented by the change in the measured carbon dioxide concentration over a lengthy period of time of up to approximately 150 days.

Various methods for measuring have been proposed. According to a first method, a gas sample is withdrawn from a sample bottle. Next the $CO_2$ concentration is determined by means of gas chromatography. This method is however very labour intensive, errors being able to occur during transference of the gas sample into the gas chromatograph. In addition, the atmosphere above the sample is affected by the gas sample withdrawal. Furthermore, the withdrawal syringe must be decontaminated and disposed of after each sample withdrawal.

In a further proposed method, a gas sample is withdrawn from the sample bottle by means of a closed pump system which contains a gas analyser. The atmosphere of the sample bottle is hereby likewise changed. During testing of a plurality of samples, the closed pump system must be decontaminated in a technically complex manner after each measurement.

It is known furthermore to detect the produced $CO_2$ through the wall of the sample bottle. For this purpose, the sample bottle is placed in the radiation path of an infrared absorption measuring unit. The $CO_2$ concentration is determined by the weakening of the radiation in a characteristic wavelength, for example 4.24 $\mu$m. In this method, there are however high demands made on the bottle quality with respect to wall thickness and to the material, which results in high costs.

In addition, the measuring result can be falsified by means of moisture being condensed-out. By means of agitation of the bottles, the bottle inner walls can be soiled which in turn impairs the measurement. Thus, quantitative measurements are only possible with high technical complexity and high costs.

Finally, it is proposed in EP 0 425 587 B1 to use optical sensors, for example based on fluorophores in order to measure the $CO_2$ concentration. The corresponding sensitive membrane is thereby introduced into the container to be tested, for example on the base, on the wall or integrated into a measuring chamber which is in contact with the sample bottle by means of diffusion with the help of a cannula. The optical properties of the membrane are monitored externally. It is however disadvantageous that the optical properties of the sensor can be impaired by other gases ($NH_3$, alcohols, . . . ) and that the long term stability of the sensors is inadequate.

With the known methods, long-lasting and trouble-free quantitative measurements of gas concentrations in closed or open systems are therefore implementable either only in an unreliable manner or technically only in a very complex manner.

The object therefore underlying the invention is to produce a method of the generic type and a device for implementing the method so that gas analyses and in particular quantitative measurements of gas concentrations can be implemented over a long period of time, in a trouble-free manner and economically.

SUMMARY OF THE INVENTION

The object is achieved according to the invention with the above-indicated method of the generic type in that at least one radiation source and at least one detector device are fixed to the measuring chamber in a defined orientation and in that the measuring radiation emitted from the radiation source proceeds at least once through the measuring chamber and is detected by the detector device after leaving the measuring chamber. With this method, the sample atmosphere to be measured from the sample system containing a sample which passes by diffusion into the separate measuring chamber, is traversed at least once by the measuring radiation in the measuring chamber. Neither withdrawal of the gas sample itself nor a measuring or detector device is thereby required within the measuring chamber. The diffusion seal is effected by sealing relative to the surrounding atmosphere so that short term and also continuous, longer lasting measurements are reliably possible without impairment from moisture or pollutants. The production of the diffusion seal between the sampling atmosphere contained in a sample system and a measuring chamber via a measuring adapter, which is separable from the sensor device, is not restricted to a specific sample system but rather many types of different sample systems are suitable, such as sample bottles or beaded rim bottles, and also open sample systems, such as pipes and the like for a measurement within the scope of the method according to the invention. Finally, the method permits the assignment of different sensor devices to different measuring adapters and measuring chambers.

In order to diffuse the sample atmosphere out of the sample system into the measuring chamber, a diffusion pipe, a cannula or simple openings, which are configured in a measuring chamber base of a measuring chamber fixed in a bottle neck as a stopper, can be used. The measurement itself is implemented after setting the diffusion equilibrium between the gas in the measuring chamber and the sample atmosphere.

The method offers in this manner a simple and economical possibility of quantitatively analysing the sample atmosphere. Complex pump devices and the like, which in fact could be used repeatedly but which would require to be decontaminated after each use, are not required. Because of the preferably one-off use of the measuring adapter which can be produced economically as a mass-produced article (disposable article), cross contamination of different samples is ruled out. In order to counteract condensing-out of moisture in the measuring adapter, the measuring adapter can be heated with a required quantity of heat.

In order to achieve the object, it is furthermore provided that, in the case of an above-indicated device of the generic type, the radiation source and the detector device can be fixed according to the invention to the measuring chamber in a defined orientation, that the measuring chamber is delimited by at least one cover which is permeable for a measuring radiation of the radiation source, and that the measuring radiation emitted from the radiation source is detected by the detector device after passing through the measuring chamber. This device does not require sensors or other measuring devices in the measuring chamber since, outwith the measuring chamber, a change in the measuring radiation is established after said measuring radiation has passed through the measuring chamber. The defined arrangement of the radiation source and of the detector device in the measuring chamber hereby ensures an exact, reproducible measuring result, it being expedient if the measuring chamber is contained in a measuring adapter which can be fixed to the sample system. It is possible with the device to produce a diffusion connection to any sample system by means of a simple, cheap measuring adapter so that the respective sample atmosphere can pass from the sample system into the measuring chamber without withdrawal of the gas sample. In the measuring chamber, the sample atmosphere is maintained separately from the surrounding atmosphere and can be measured by the separate sensor device, which is disposed outwith the measuring chamber, and can be quantitatively analysed.

It is particularly advantageous that the radiation source and the detector device are disposed in one sensor head which can be coupled to the measuring adapter. By means of the removable sensor head, many identical or different sample systems or sample atmospheres can be tested with only one sensor head.

The measuring adapter can remain in diffusion contact with the sample system on a long-term basis, for example several weeks, the measurement being able to be implemented with a sensor head continuously or intermittently.

The measuring adapter can preferably contain the measuring chamber. Likewise, it is expedient that the radiation source is contained in the measuring adapter also together with the measuring chamber.

It is expedient for any coupling if the measuring adapter has a universal joint for different sample systems. Such a measuring adapter can be used as a disposable measuring adapter because of its economical production. Complex decontamination of the measuring device is therefore unnecessary.

The measuring adapter can thereby equally be coupled to open sample systems, such as for example pipes.

The measuring chamber can be configured in different ways and be disposed in different positions relative to the radiation source and to the detector device. For example the measuring chamber contains a first radiation-permeable cover or disc at the entrance of the measuring radiation into the measuring chamber and a second radiation-permeable cover at the et of the measuring radiation from the measuring chamber. The measuring radiation enters through the first disc into the measuring chamber and leaves it after traversing through the second cover in the direction of the detector device. If the first cover and the second cover are disposed approximately opposite each other in the measuring chamber, the measuring radiation can traverse the measuring chamber in a straight path, the measuring chamber being able to be disposed in particular between the radiation source and the detector device. On the other hand, the measuring radiation can also be directed by optical elements from the radiation source to the measuring chamber and/or from the measuring chamber to the detector device so that different arrangements of the radiation source and of the detector device can be chosen.

In a further embodiment, the measuring chamber is delimited on one side by the permeable cover, which is adjacent to the radiation source and the detector device, and on the other side by a measuring chamber wall, which reflects the measuring radiation, so that the measuring radiation emitted from the radiation source is reflected towards the detector device after passing through the measuring chamber. The radiation source and the detector device can be disposed thereby in the sensor head next to each other with approximately parallel emergence of the measuring radiation from the radiation source and entrance of the measuring radiation into the detector device.

In a preferred configuration, the measuring chamber opens in a funnel or pyramid shape towards a coupled-on sensor head and the measuring chamber walls reflect the measuring radiation. A double reflection of the measuring radiation is hereby produced on the oppositely-situated funnel walls.

A further preferred embodiment provides that the reflecting measuring chamber wall is a lower reflection plate, which is parallel to the upper cover and has openings as a diffusion t. The radiation source and the detector device can hereby be disposed at an angle relative to each other so that the measuring radiation is directed from the reflection plate directly to the detector device. This configuration is particularly advantageous when the measuring adapter is formed as a stopper for a sample bottle, which stopper can be inserted in particular into a bottle neck of the sample bottle. A sample bottle of this type is for example a standard beaded rim bottle. The length of the measuring chamber can hereby be relatively large so that gases with a low absorption coefficient can be quantitatively monitored by means of the long path of the measuring radiation through the measuring chamber.

A diffusion seal can be formed in the described measuring chambers in that the reflecting measuring chamber wall or reflection plate has at least one opening, the opening diameter being decisive for the time required for adjusting the diffusion equilibrium.

In a further embodiment, the sample system or the sample bottle is sealed with an elastomer seal and the diffusion seal of the measuring adapter is a cannula for penetrating the seal. The dimension or the diameter of the measuring chamber is hereby not dependent upon the dimension of the bottle neck or restricted thereto. In order to achieve equilibrium between the sample atmosphere and the gas atmosphere in the measuring chamber in as short a time as possible, it is expedient to configure the diameter of the cannula to be as big as possible, its length to be as short as possible and the volume of the measuring chamber to be as small as possible. The optimal dimensions are determined by the kinetics of the sample to be tested.

When using at least two radiation sources, one source can be used as reference for compensating for the ageing of the other radiation sources since it is not so frequently operated and hence the ageing is negligible. This is possible in principle with any gas concentration.

If the sensor device has at least two radiation sources, the measuring process can be continued essentially without interruption upon failure of one radiation source, after for example an automatic switching to the second radiation source.

Furthermore, the sensor device can have at least two detector devices so that a reference measurement can be implemented at the same time. The radiation source irradiates both detectors to the same extent (same light path), the one detector delivering a concentration-dependent signal in the case of the presence of the gas concentration to be measured whilst the other detector serves only as a reference and hence delivers no concentration-dependent signal.

The measuring adapter and the sensor head which are configured as separate components of the device according to the invention are expediently placed in a defined position relative to each other in order to implement a measurement above their housing or an integrated positioning unit and subsequently are connected in a mechanically stable manner to each other by means of a coupling de vice. It is thereby advantageous if the coupling device is provided essentially on the sensor head since in this case the measuring adapter is constructed in a simpler fashion and can be produced more economically. The coupling device can be disposed also exclusively on the sensor head or it can be a separate component.

A broad-band thermal radiator, LEDs (light emitting diodes), diode lasers and in particular infrared radiators or UV light radiators can be provided as the radiation source.

The radiation-permeable cover or disc can be formed from lime-soda glass, boron silicate glass, quartz glass, silicon or sapphire, calcium fluoride ($CaF_2$), barium fluoride ($BaF_2$), germanium (Ge) or zinc selenide (ZnSe).

For a multiplicity of application possibilities, sensor heads, which are provided with different sensor devices, can be provided for coupling to the measuring adapter or adapters. The gas concentration measurement by a sensor device in the measuring chamber is implemented preferably by means of gas-specific absorption of electromagnetic radiation. The measuring adapter is hereby configured in such a manner that the electromagnetic radiation emitted from the sensor head enters into a reciprocal effect in the measuring chamber with the sample atmosphere which is diffused therein and then can be detected by the sensor head.

By means of the defined positioning of the sensor head relative to the measuring adapter and because of the mechanically stable coupling of co both components, it is not necessary to recalibrate before each measurement. In addition, because of the simple and mass-produced configuration of the measuring adapter, for example as a plastic injection moulded part, no further calibration is required for structurally similar measuring adapters after a single type calibration of the sensor head with a measuring adapter.

BRIEF DESCRIPTION OF THE INVENTION

Figure 2:
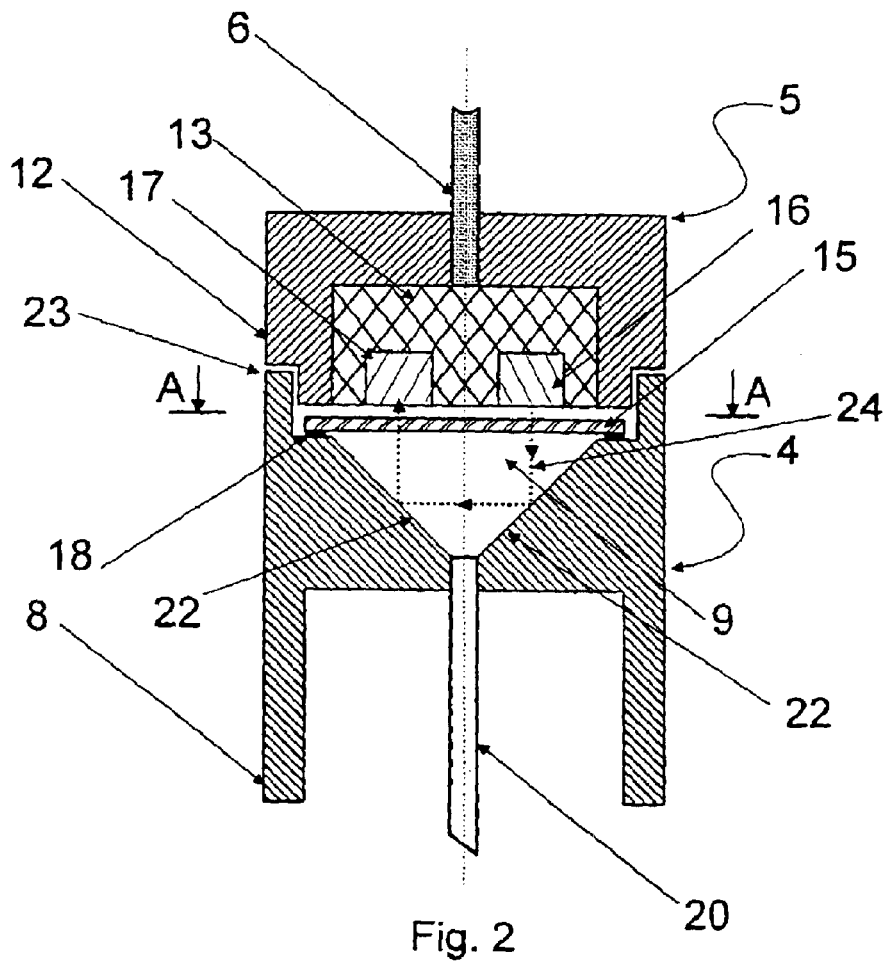
Figure 3:
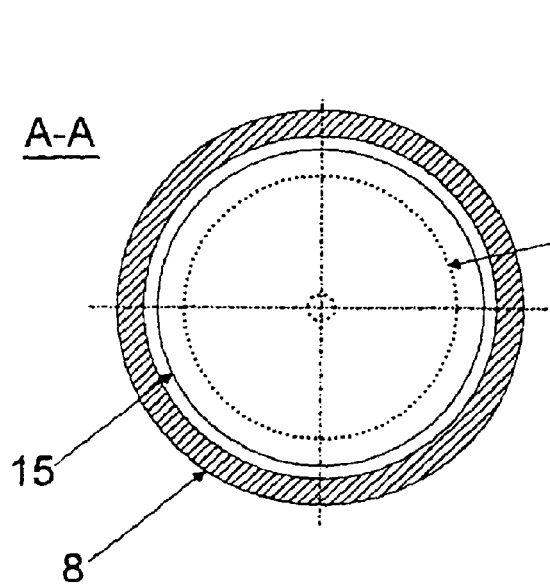
Figure 4:
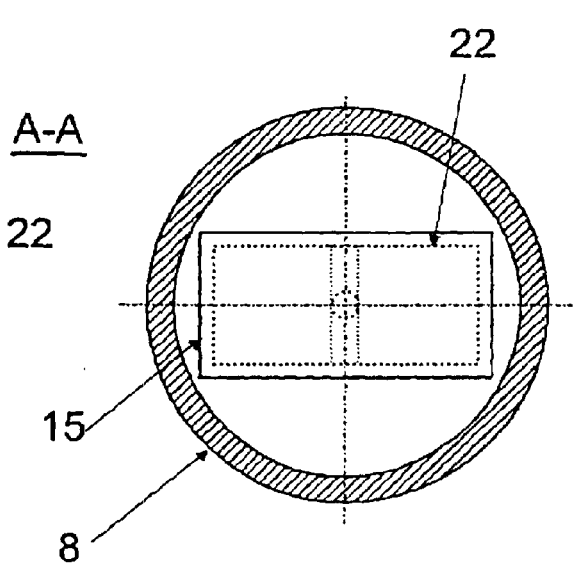
Figure 5:
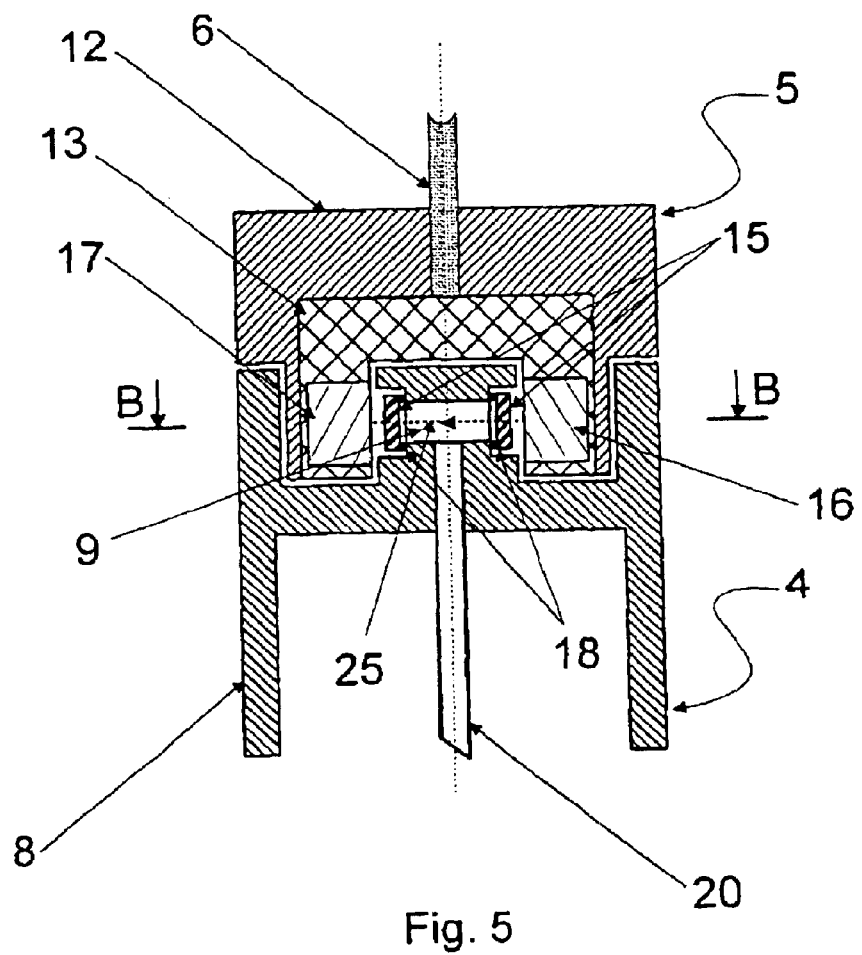
Figure 6:
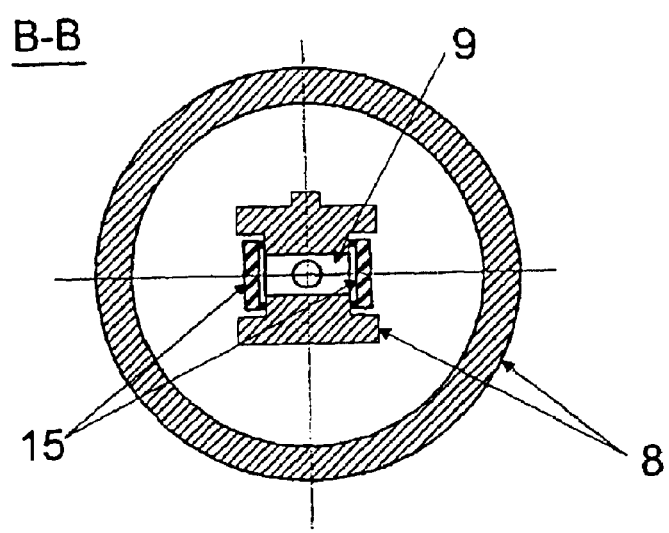
Figure 7:
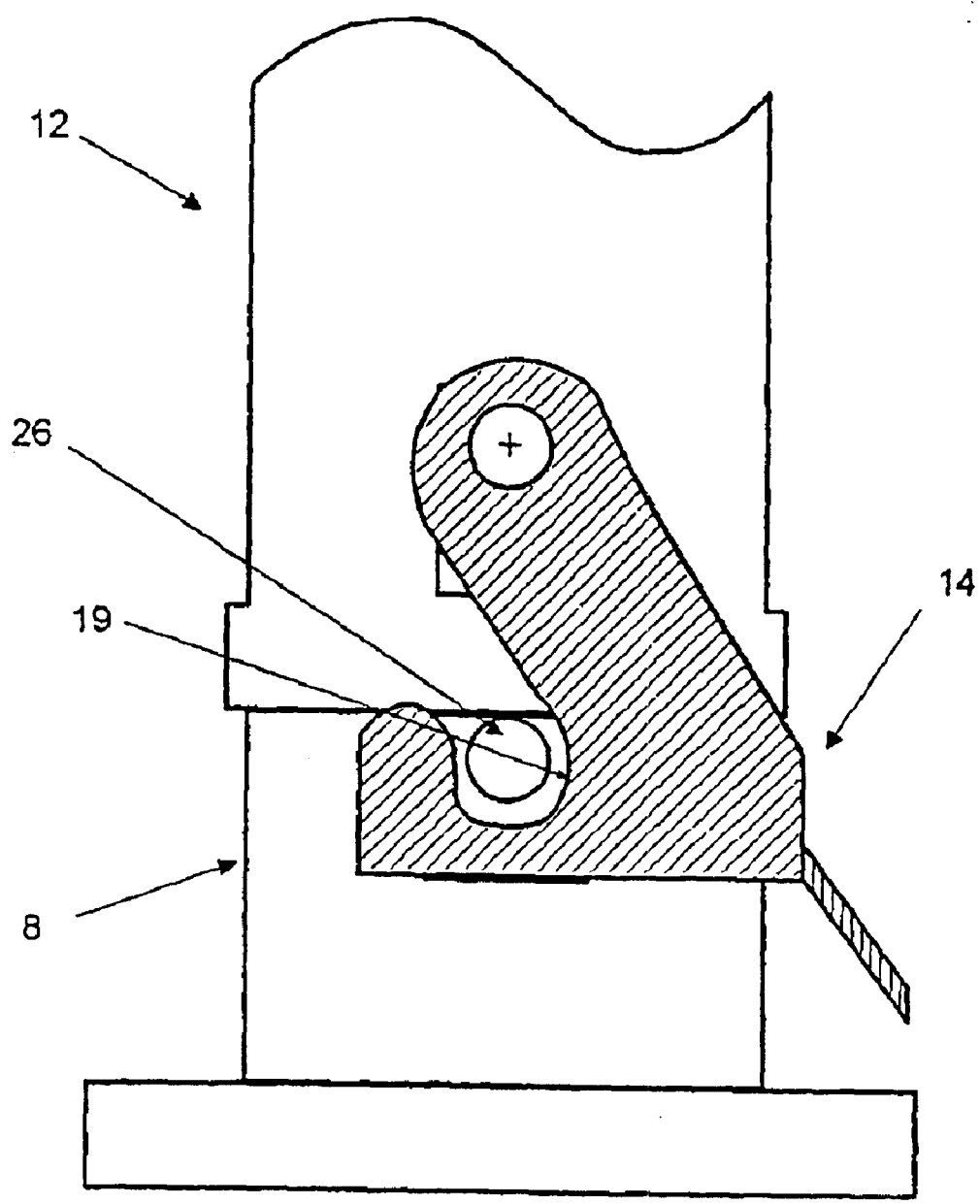
Figure 8:
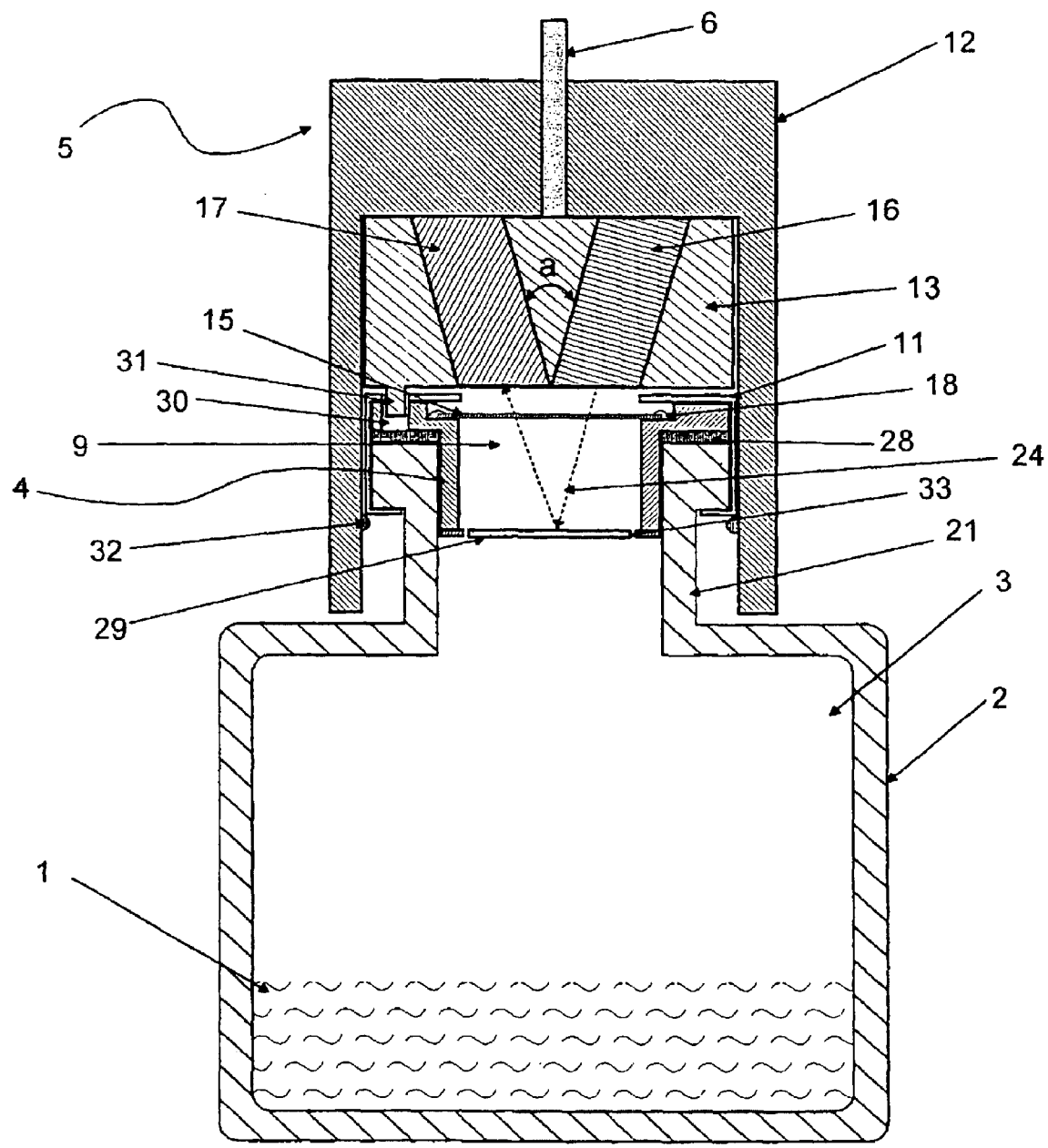
Figure 9:
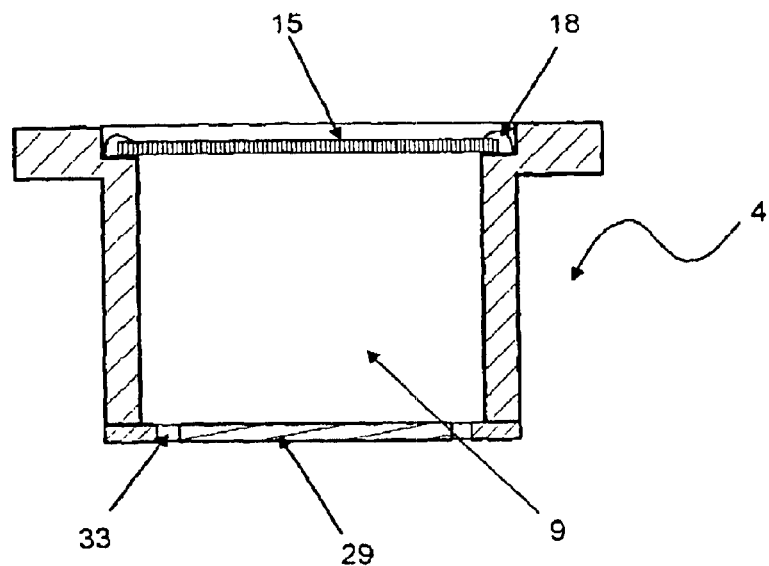
Figure 10:
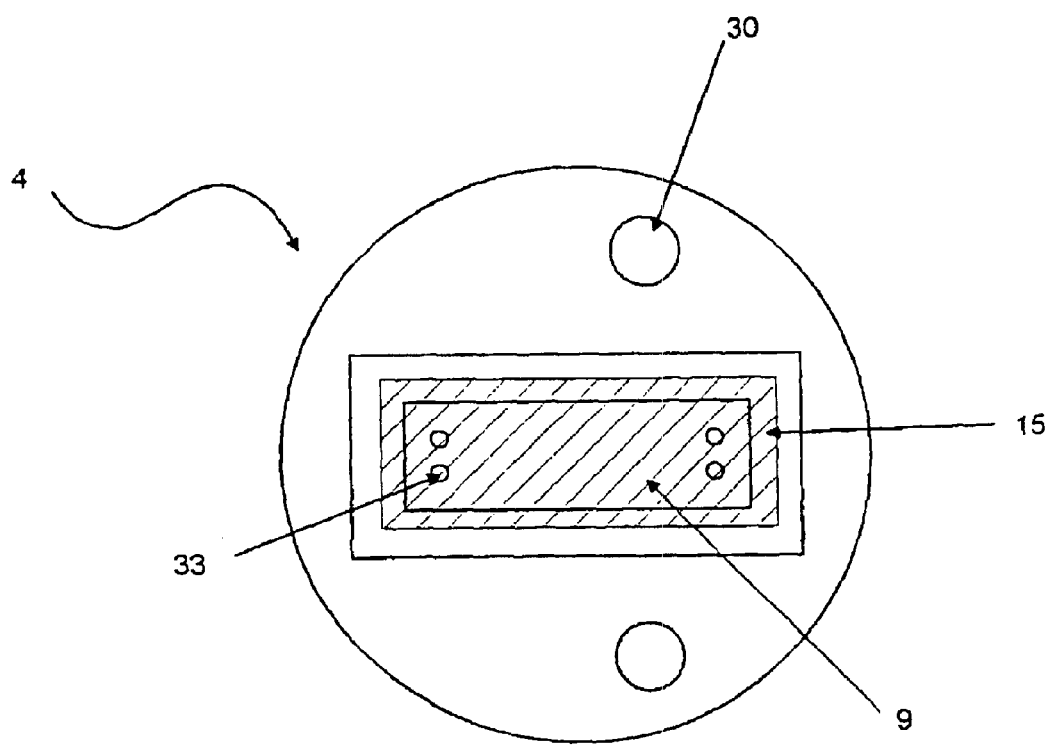
Figure 11:
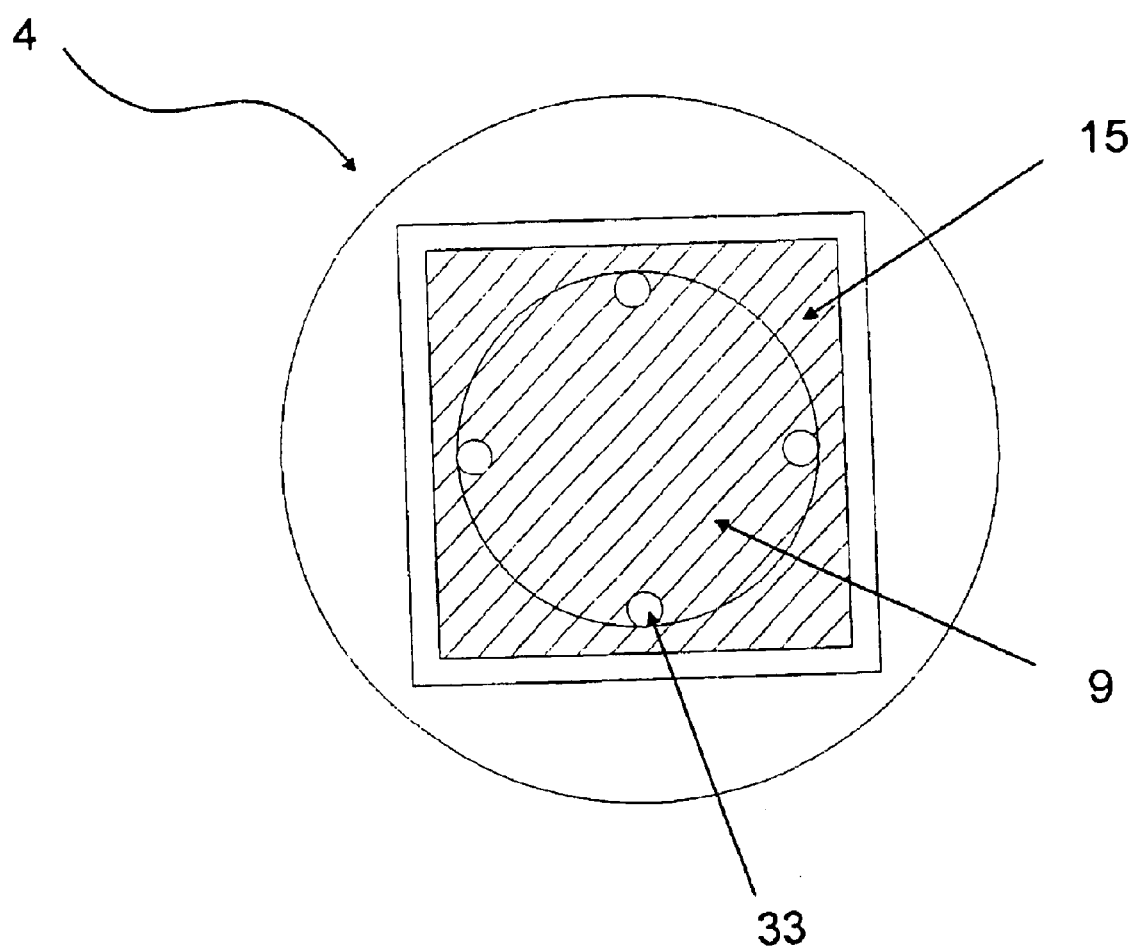
Figure 12:
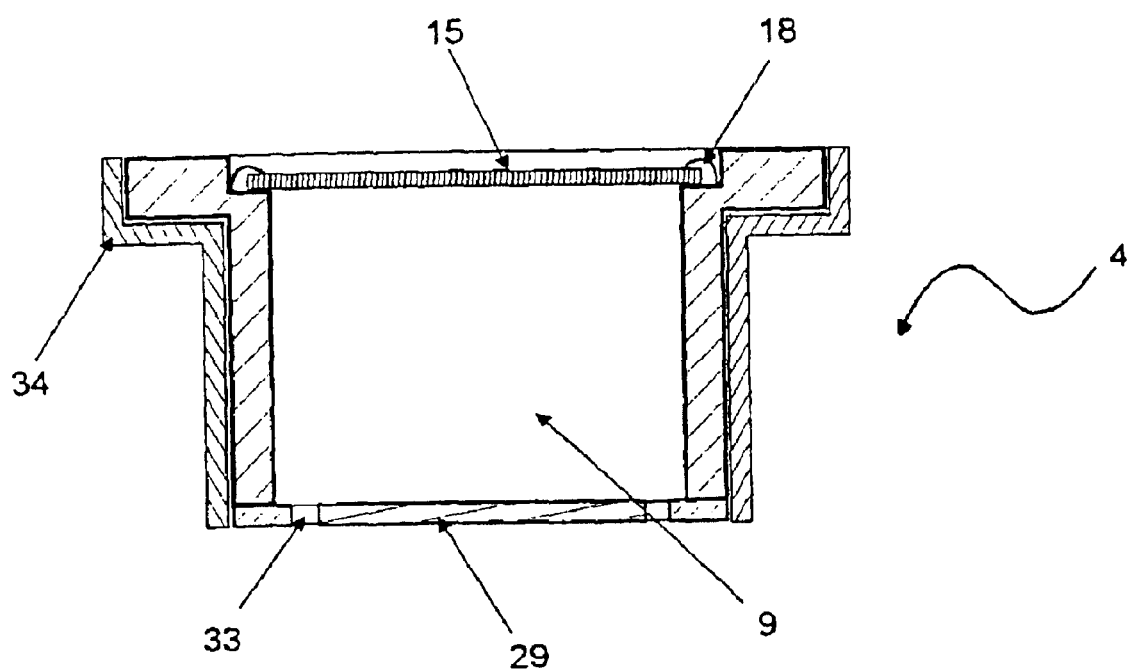
Figure 13:
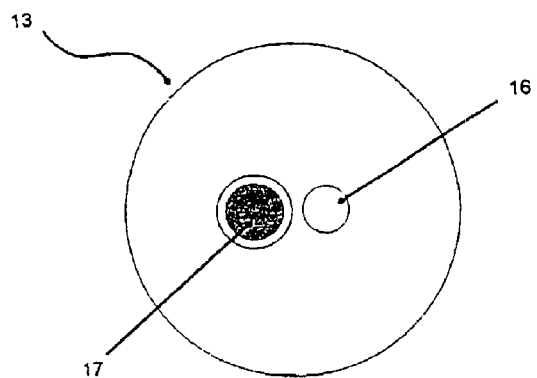
Figure 14:
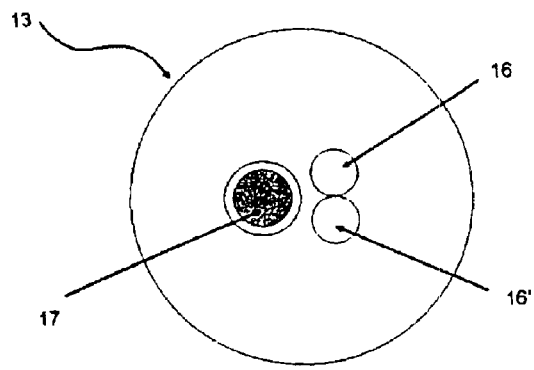

The invention is explained in more detail subsequently with reference to embodiments, given by way of example, and with reference to drawings which show:

FIG. 1 a device according to the invention on a sample bottle in a side view in section and in schematic representation;

FIG. 2 an embodiment of the device according to the invention in a sectional view;

FIG. 3 the measuring adapter of the device in a sectional view along the plane A—A in FIG. 2;

FIG. 4 a further embodiment of the measuring adapter of the device in a sectional view along the plane A—A in FIG. 2;

FIG. 5 a further embodiment of the device according to the invention in a sectional view;

FIG. 6 the measuring adapter of the device in a sectional view along the plane B—B in FIG. 5;

FIG. 7 the device with a coupling device in a plan view;

FIG. 8 a further embodiment of the device according to the invention in a sectional view;

FIG. 9 the measuring adapter of the device in a sectional view;

FIG. 10 an embodiment of the measuring adapter of the device in an upper plan view;

FIG. 11 a further embodiment of the measuring adapter of the device in an upper plan view;

FIG. 12 the measuring adapter with a seal in a sectional view;

FIG. 13 an embodiment of the sensor head of the device in a view from below;

FIG. 14 a further embodiment of the sensor head of the device in a view from below; and FIG. 15 a further embodiment of the sensor head of the device in a view from below.

Figure 16:
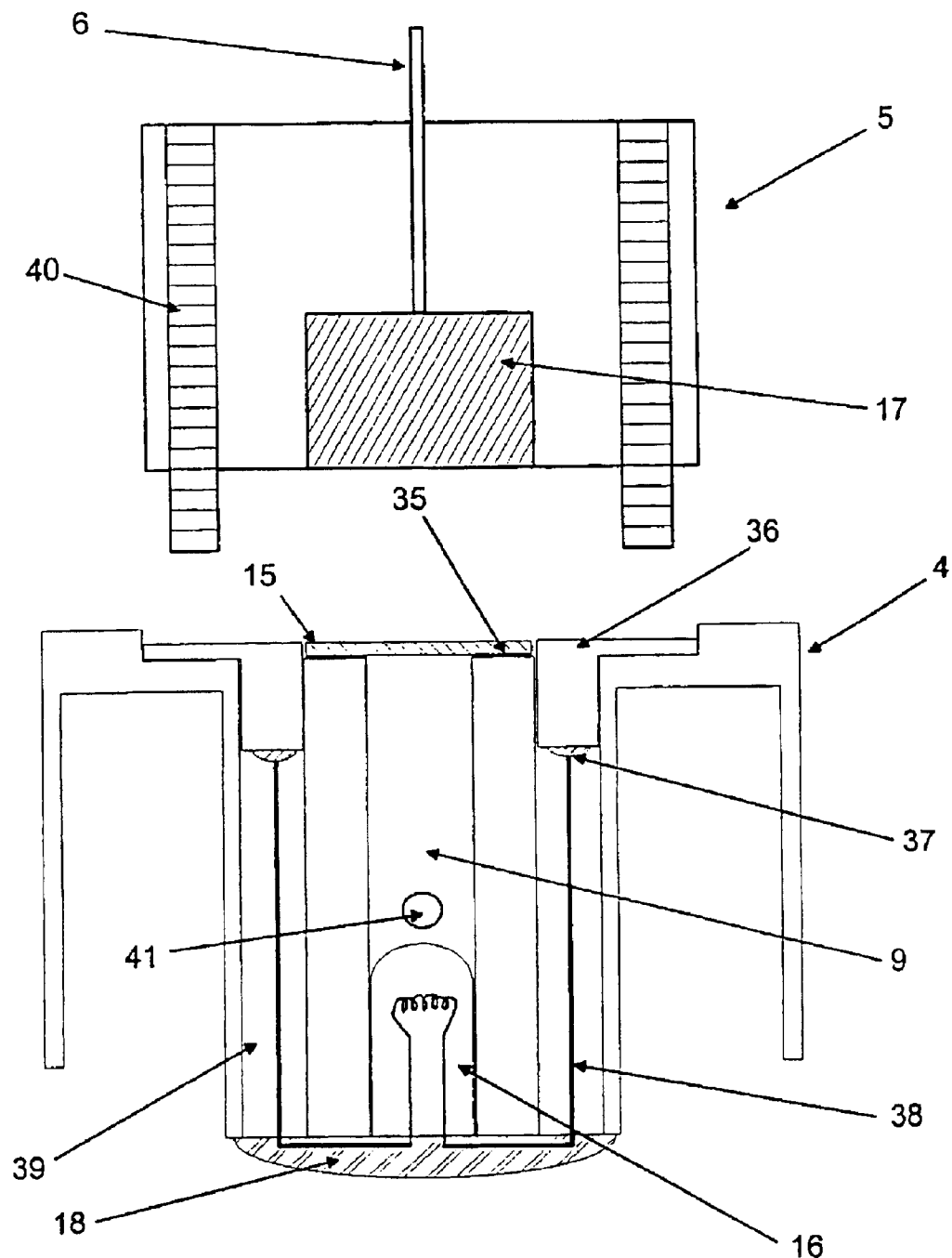

FIG. 16 a further embodiment in which the measuring adapter contains the radiation source, in a side view in section.

Figure 17:
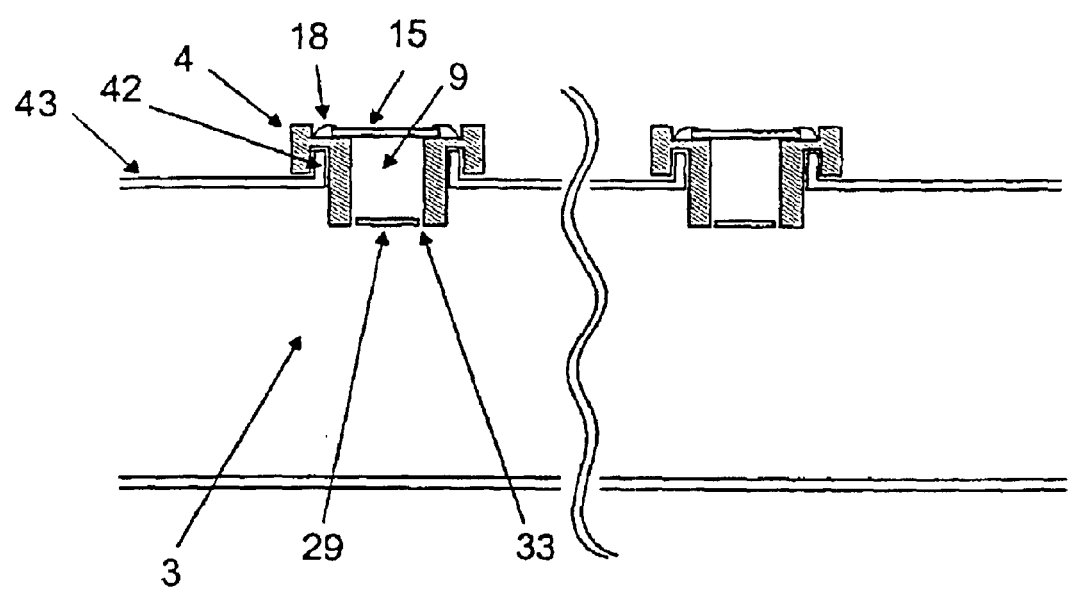

FIG. 17 a further embodiment in which the adapter is fixed to a pipe in a sectional view.

Figure 18:
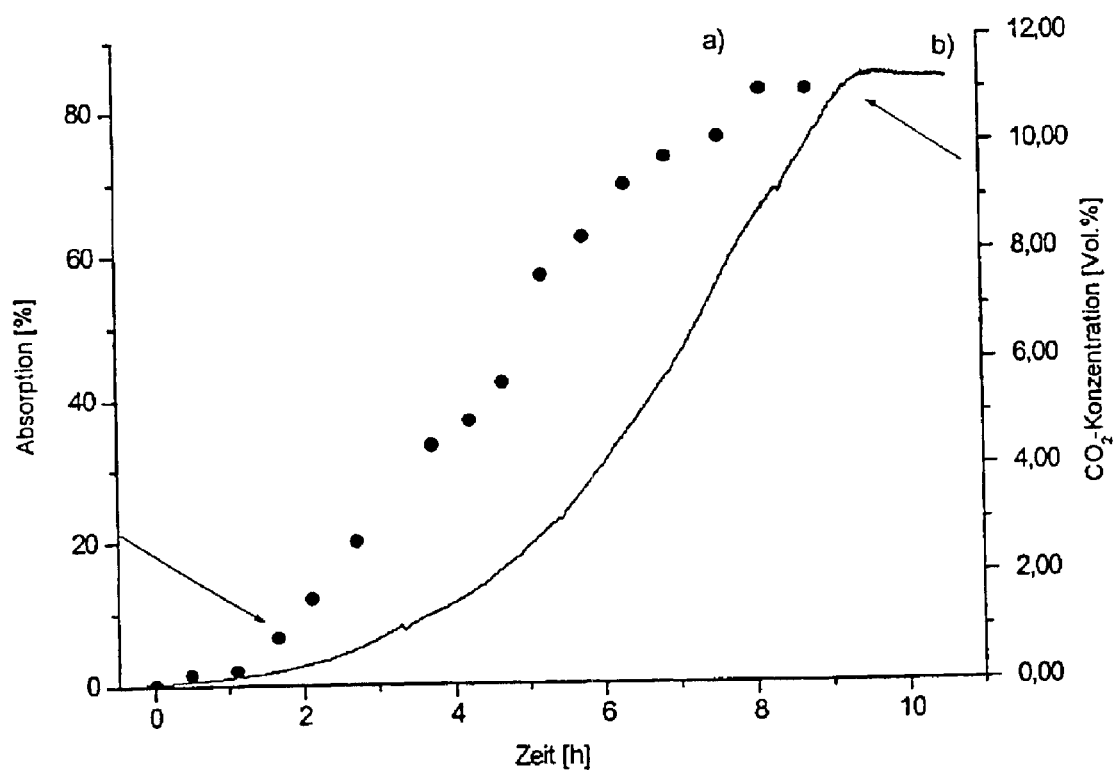

FIG. 18 a measurement curve of the device according to the invention for monitoring the $CO_2$ production of a yeast culture.

A solid, semi-solid, liquid or gaseous sample 1 to be tested is situated in a sample bottle 2 which is securely sealed by an elastomer seal, for example LA a septum 10, and a flanged cap 11 which is fixed to the bottle neck 21. Within the sample bottle 2, a sample atmosphere 3 is formed above the sample 1.

DETAILED DESCRIPTION OF THE PREFERRED EMBODIMENT

An embodiment of the device according to the invention for the quantitative gas analysis contains a measuring adapter 4 and a sensor head 5 which is connected by a flexible cable 6 to an electronic measuring and control device 7. The measuring adapter 4 has a housing 8 with which it is fixable on the sample bottle 2 and also a measuring chamber 9, which is configured in the housing 8, and a cannula 20 which is connected to the measuring chamber 9. When fixing the measuring adapter 4 on the sample bottle 2, the cannula 20, after piercing the septum 10, produces a seal between the interior of the sample bottle 2 and the measuring chamber 9 so that the sample atmosphere 3 can pass into the measuring chamber 9 by means of diffusion. The gas atmosphere within the measuring chamber 9 is consequently situated in a diffusion equilibrium with the sample atmosphere 3 in the sample bottle 2. The time required for setting the equilibrium is determined essentially by the length and the cross-sectional area of the cannula 20 and the volume of the measuring chamber 9. In order that the temporal detection of the change in the sample composition is ensured, the time T must be smaller than the temporal changes in the sample composition. This condition is taken into account in the constructional design of the cannula 20 and of the measuring chamber 9.

The measurement of the gas concentration in the measuring chamber 9 is effected by means of the sensor head 5 which has a coupling device 14, such as for example a screw connection illustrated in FIG. 1 which ensures a firm connection between the sensor head 5 and the measuring adapter 4. The sensor head 5 contains a housing 12 with a sensor device 13 which is assigned to the measuring chamber 9 and enables continuous or quasi-continuous contact-free measurement and monitoring of the concentration and composition of the gas atmosphere in the measuring chamber 9, as a result of which conclusions can be drawn about the C, properties of the sample 1 in the sample bottle 2.

FIG. 2 illustrates an embodiment of the measuring chamber 9 and of the sensor device 13 of the device according to the invention. The sensor device 13 contains a radiation source 16 for producing electromagnetic radiation in the relevant spectral range and a detector device 17 for detecting the residual radiation after passing through the measuring chamber 9. The radiation source 16 and the detector device 17 are constructed in such a manner that preferably only the selective wavelength-specific weakening of the radiation intensity is measured by the interaction with the gas molecules to be detected in the measuring chamber 9. For this purpose, a wavelength selecting element, for example an optical filter, can be disposed for example in the measuring radiation distance or measuring light distance (illustrated schematically as measuring radiation or radiation path 24) between the radiation source 16 and the detector device 17.

The measuring chamber 9 is covered on its upper side which is orientated towards the detector device 17 with a window which is permeable for the measuring radiation, in particular optical window 15 which can be sealed or fixed in a gas-tight manner on the housing 8 by means of a seal 18 which can also be an adhesive. The optical window 15 is formed from a material which is transparent in the relevant spectral range. The window 15 can be formed for example from a piece of monocrystalline silicon and can also have an anti-reflection layer. The internal walls 22 of the measuring chamber 9 are configured and processed in such a manner that a reflection and extension of the radiation emitted from the radiation source 16 towards the detector device 17 is ensured. Thus the reflecting walls 22 of the measuring chamber 9 can be disposed at an angle of 45° relative to the direction of the emitted and reflected radiation 24, as is illustrated in FIG. 2.

By means of defined contact faces between the measuring adapter 4 and the sensor head 5, which are formed for example as surrounding shoulders 23 which are assigned to each other, a detachable and nevertheless mechanically secure, stable and reproducible orientation and positioning of the sensor head 5 on the measuring adapter 4 and hence of the sensor device 13 on the measuring chamber 9 is achieved. The precision of this coupling which results from a high-quality mechanical processing of the contacting faces ensures quantitative gas concentration measurements in the measuring chamber 9 even after multiple coupling and uncoupling of the sensor head 5 on the measuring adapter 4.

FIG. 3 shows the measuring adapter 4 according to FIG. 2 with a conical or funnel-shaped measuring chamber 9 in which the conical angle of the walls 22 is 90° and which is covered with a round window 15.

FIG. 4 shows a further embodiment of the measuring adapter 4 according to FIG. 2 with a measuring chamber 9 illustrated in plan view, which is rectangular on the upper side, with two flat walls 22, which reflect the incident radiation 24 towards the detector device 17 and stand in a wedge shape at a wedge angle of 90° relative to each other. The measuring chamber 9 is covered by a rectangular window 15.

In the embodiment illustrated in FIG. 5 of the device according to the invention, the radiation source 16 of the sensor device 13 and the detector device 17 are disposed on an optical axis 25 at a spacing from each other and situated opposite each other. The measuring chamber 9 has a tubular configuration and is sealed in a gas-tight manner by two oppositely-situated optical windows 15. If the sensor head 5 is disposed on the measuring adapter 4, the measuring chamber 9 is disposed between the radiation source 16 and the detector device 17 and orientated along the optical axis 25.

FIG. 6 shows the housing 8 of the measuring adapter 4 according to FIG. 5 with the tubular measuring chamber 9 and both windows 15.

FIG. 7 shows an embodiment of the coupling device 14 as a sealing part which is mounted pivotally on the housing 12 of the sensor head 5 and which is lockable with a recess 19 on a pin 26 on the housing 8 of the measuring adapter 4 in order to retain the sensor head 5 on the measuring adapter 4 locked in a defined position.

The material of the windows 15 which are used is produced in such a manner that the electromagnetic radiation can fall through the window 15 onto the detector device 17. Lime-soda-glass and also boron silicate glass are suitable up to a wavelength range of approximately 5 $\mu$m and quartz glass is also suitable up to approximately 2.5 $\mu$m. For higher wavelength ranges, silicon or sapphire (up to 6.7 $\mu$m) can be used as the window or disc material. Furthermore calcium fluoride ($CaF_2$), barium fluoride ($BaF_2$), germanium (Ge) or zinc selenide (ZnSe) can be used. The optical filter can also be used as the window material. In addition, the windows used can be provided with an anti-reflection layer.

By means of the length of the radiation path 24 or the light path of the light beam in the measuring chamber 9, the concentration range of the gas to be detected can also be prescribed. Thus a measuring chamber can be used in the quantitative measurement of low gas concentrations, in which chamber the light path is lengthened by multiple reflections. A multiplicity of different arrangements is suitable for this purpose.

A further embodiment of the invention is illustrated in FIGS. 8 to 10. The measuring adapter 4 is formed in the manner of a stopper for the sample container 2 which is for example a beaded rim bottle (see FIG. 8). The measuring chamber 9 is for example cylindrical or rectangular in cross-section and is disposed in the bottle neck 21 of the beaded rim bottle. The underside of the measuring chamber 9 which extends into the bottle neck 21 is sealed by a cover or plate 29, which reflects the measuring radiation and in which one or more openings 35 are configured on the edge side, which openings form a diffusion seal 33 and through which the gas to be detected can pass from the sample bottle 2 into the measuring chamber 9.

On the upper side of the measuring adapter 4, the measuring chamber 9 is covered by a cover which is permeable for the measuring radiation, such as for example an optical window 15 which is secured and sealed thereon with a seal or with an adhesive 18. When applying the measuring adapter 4 to the sample bottle 2, a seal 28 is placed on the bottle neck 21 on which seal a flange of the measuring adapter 4 is placed. A flanged cap 11 encompasses the bottle neck 21 and is fixed both to the lower edge of the bottle neck and also to the flange upper side by beading.

The sensor head 5 contains an approximately pot-shaped housing 12 for placing on the bottle neck 21. The internal diameter of the housing wall is adapted to the flanged cap 11 in such a manner that it offers a guide for the sensor head 5. In the interior of the housing 12, the sensor device 13 is contained with a radiation source 16 for producing electromagnetic measuring radiation and with a detector device 17 for receiving the measuring radiation. A flexible cable 6 connects the sensor device 13 to an electronic measuring and controlling device 7 corresponding to the previous example. The radiation source 16 and the detector device 17 are disposed relative to each other at an angle at in such a manner that the measuring radiation emitted by the radiation source 16 from the reflecting plate 29 to the detector device 17 is reflected according to the schematically illustrated radiation path 24. If the measuring chamber 9, as is illustrated in FIGS. 2–4, is configured with a conical shape or a funnel shape, the angle α between the detector device 17 and the radiation source 16 is zero degrees. The sensor device 13 has a projecting pin 31 which engages in an assigned recess 30 in the measuring adapter 4 and hence enables exact positioning of the sensor device on the adapter 4. The flanged cap 11 also has an opening in the region of the recess 30. A stopping mechanism 32 is integrated on the housing internal wall and engages under the bottle neck edge for fixing the sensor head 5 to the measuring adapter 4. Because of the short diffusion distances, the length of which is established by the thickness of the plate and is for example 0.5 mm, the sample atmosphere 3 can diffuse quickly from the sample bottle 2 into the measuring chamber 9 so that even rapid kinetic processes can be monitored. The measuring adapter 4 can have a measuring chamber 9 with a large length, i.e. formed with a large spacing between the optical disc 15 and the reflecting plate 29. Because of the long path of the measuring radiation 24 through the measuring chamber 9, gases with a low absorption coefficient can be quantitatively monitored.

The measuring adapter 4 is an injection moulded part which can be produced simply and economically, having an adhered optical window which is formed for example from silicon and can be provided with an anti-reflection layer.

If the measuring chamber 9 in the measuring adapter 4, which is configured as a stopper, is configured to be round instead of channel-shaped, then no positioning device is required since all the parts are disposed symmetrically relative to each other (FIG. 11).

The measuring adapter 4 can be integrated directly into a rubber seal 34 which surrounds said adapter for example in a shell-like manner on the circumference or is an applied coating with a sealing effect so that additional application of a seal is not required (FIG. 12).

The sensor device 13 illustrated in FIG. 13 in a view from below contains a detector 17 and a radiation source 16.

In FIG. 14, a detector 17 and two radiation sources 16 and 16' are integrated into the sensor device 13. Here, a radiation source 16 is used as measuring source and the other radiation source 16' is brought into play at specific time intervals as a reference source for compensating for ageing of the measuring source. The radiation sources 16 and 16' are disposed symmetrically relative to the detector 17 so that, in both radiation sources 16 and 16', the same light path to the detector 17 is offered.

Figure 15:
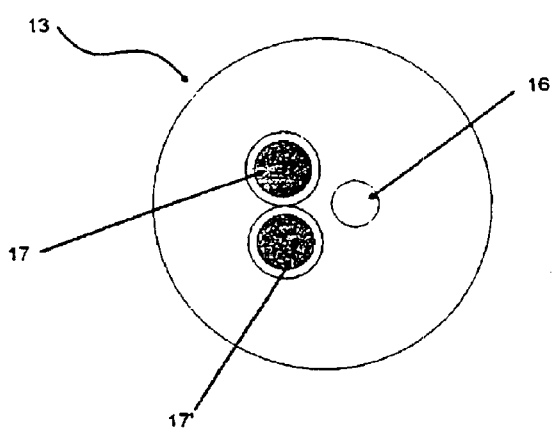

The sensor device 13 can likewise comprise two detectors 17 and 17' and a radiation source 16 (FIG. 15). One detector is thereby used for measuring the relevant gas concentration and the other detector as reference.

In the described embodiments the selective, quantitative detection of a specific gas or also of a plurality of gases can be achieved by choice of radiation receiver or receivers or detector devices 17 and of one or more radiation sources 16. The selectivity of the radiation receivers can be, ensured by the choice of specific interference filters. The interference filters can for example be light-permeable only at specific wavelengths, such as for example at 4.24 μm for carbon dioxide ($CO_2$), at 3.4 μm for hydrocarbons, at 5.3 μm for NO, at 10.9 μm for freon etc. The interference filters can also be disposed in front of one or in front of a plurality of radiation sources. As radiation sources, for example broadband thermal radiators, LEDs (light emitting diodes), diode lasers, infrared radiators or UV light radiators can be used.

FIG. 16 shows a further embodiment. Here, the sensor head 5 comprises only the detection device (17), for example a single detector, double detector, double detector with beam splitter and the contact pins (40), whilst the radiation source (16) is situated in the measuring adapter. These contact pins touch the contact faces (36) after the sensor head has been placed on the measuring adapter (4) so that at least one radiation source is set in operation in the measuring adapter. The radiation source (16) is integrated directly into the measuring adapter (4). The measuring chamber (9) is provided with an optically permeable disc (15) and sealing mass (35). The radiation source is contacted with cables (38) on the contact faces (36) via a soldering point (37). The sample atmosphere can diffuse into the measuring chamber via diffusion seals (41). Lead-throughs (39) are provided in the measuring adapter for the cables (38). The sensor head (5) comprises a detector device (17). This can be for example a singe detector, a double detector or similar. The sensor head is connected to a measuring electronic unit via a flexible cable (6). The ms radiation source (16) is set in operation after the sensor head (14) is placed above the contact pins (40).

FIG. 17 shows an embodiment in which the measuring adapter (4) is fixed to a pipe (43). It is consequently possible that the sample atmosphere can be measured in the pipe without the sensor device coming into contact with the latter. In addition, a plurality of measuring places can be tested in succession with a sensor head. The measuring adapter, since it is conceptualised as an economical disposable article, can be replaced at any time. A plurality of measuring adapters (4) can be connected via a connection (42) to a pipe (43). This connection can be configured for example as a screw thread or a snap-on device. The sensor head of FIG. 1 can be placed on the measuring adapter for measuring the sample atmosphere (3).

FIG. 18 shows the measurement curve which can be adopted by a device according to the invention. A continuous monitoring of the growth of a yeast culture, *Candida Parapsilosis*, was thereby implemented with the developed measuring system. The $CO_2$ concentration was hereby recorded continuously. In parallel thereto, the same yeast culture was monitored every half-hour in a second tube with a photometer. Likewise, the growth of other micro-organisms, such as for example *Salmonella typhymurium* or *E. Coli* bacteria can be monitored. In general, the presence of micro-organisms which produce for example carbon dioxide can be detected with this development.

The device can also be used in order to monitor externally an internal atmosphere of a system. It is of no consequence thereby whether the system is a closed circulation or for example a pipe through which a gas flows.

What is claimed is:

1. Method for the quantitative gas analysis in which the gas analysis of a sample atmosphere is implemented by means of a sensor device, a diffusion seal being produced between the sample atmosphere contained in a sample system and a measuring chamber via a measuring adapter, at least one radiation source and at least one detector device being orientated on the measuring chamber in such a manner that the measuring radiation emitted from at least one radiation source proceeds at least once through the measuring chamber and is detected by at least one detector device after leaving the measuring chamber, characterised in that the measuring adapter can be coupled to the sample system and a sensor head is used which can be coupled to the measuring adapter and in which at least one detector device is disposed.

2. Method according to claim 1, further comprising the step of heating the measuring adapter.

3. Method according to claim 1 wherein the measuring adapter is used only once in order to avoid cross-contaminations.

4. Device for the quantitative gas analysis of a sample atmosphere, which is contained in a sample system, with a measuring adapter, which contains a measuring chamber, a diffusion pipe, a cannula or at least one opening in the measuring chamber wall as diffusion seal for the diffusion of the sample atmosphere into the measuring chamber, a radiation source and a detector device, the measuring chamber being delimited by at least one cover, which is permeable for a measuring radiation of the radiation source, and the radiation source and the detector device being disposed on the measuring chamber in such a manner that the measuring radiation emitted from the radiation source is detected by the detector device after passing at least once through the measuring chamber, characterised in that the measuring adapter can be coupled to the sample system and that at least one detector device is disposed in a sensor head which can be coupled to the measuring adapter.

5. Device according to claim 4, wherein the measuring chamber is contained in the measuring adapter.

6. Device according to one of the claim 4 wherein the radiation source is contained in the measuring adapter.

7. Device according to claim 4 wherein the measuring adapter is configured as a stopper.

8. Device according to claim 4 wherein the measuring adapter has a flanged connection.

9. Device according to claim 4 wherein the measuring adapter has a screw thread.

10. Device according to claim 4 wherein the measuring adapter has a snap-on device.

11. Device according to claim 4 wherein the measuring adapter contains a diffusion pipe as diffusion seal.

12. Device according to claim 4 wherein the measuring adapter contains a cannula as diffusion seal.

13. Device according to claim 4 wherein the measuring adapter contains at least one opening as diffusion seal.

14. Device according to claim 4 wherein the measuring chamber is delimited on one side by the cover and on the other side by a measuring chamber wall, which reflects the measuring radiation, so that the measuring radiation emitted from the radiation source is reflected towards the detector device after passing through the measuring chamber.

15. Device according to claim 14, wherein the reflecting measuring chamber wall has at least one opening as diffusion seal for the diffusion of the sample atmosphere out of the sample system into the measuring chamber.

16. Device according to claim 14 wherein the measuring chamber opens towards the coupled-on sensor head in a funnel- or pyramid-shape in order to reflect the measuring radiation on the measuring chamber walls.

17. Device according to claim 14 wherein the reflecting measuring chamber wall is a reflection plate, which is parallel to the cover and has openings as diffusion seal.

18. Device according to claim 4 wherein the measuring chamber has the first cover between radiation source and measuring chamber and the second cover between measuring chamber and detector device.

19. Device according to claim 18, wherein the first cover and the second cover are disposed on the measuring chamber situated approximately opposite each other.

20. Device according to claim 4 wherein the measuring chamber is disposed between the radiation source and the detector device.

21. Device according to claim 4 wherein the device has optical elements such as mirrors or light guides for introducing the measuring radiation into the measuring chamber.

22. Device according to claim 4 wherein the device has optical elements such as mirrors or light guides for directing the measuring radiation, which emanates from the measuring chamber, onto the detector device.

23. Device according to claim 4 wherein in that the sensor device has at least two radiation source.

24. Device according to claim 4 wherein the sensor device has at least two detector devices.

25. Device according to claim 4 wherein a coupling device is provided for a coupling of the sensor head to the measuring adapter.

26. Device according to claim 25, wherein the sensor head has a coupling device.

27. Device according to claim 4 wherein a broad-band thermal radiator, LEDs (light-emitting diodes), diode lasers, infrared radiators or UV light radiators are provided as radiation source.

28. Device according to claim 4 wherein the radiation-permeable cover is formed from lime-soda-glass, boron silicate glass, quartz glass, silicon or sapphire, calcium fluoride ($CaF_2$), barium fluoride ($BaF_2$), germanium (Ge) or zinc selenide (SnSe).

29. Measuring system according to claim 28, wherein the measuring adapter can be coupled to a pipe as sample system.

30. Measuring system comprising a device according to claim 4 and a sample system which contains a sample atmosphere, wherein the measuring adapter has a universal joint for different sample systems.

31. Measuring system according to claim 30, wherein the measuring adapter can be coupled to a sample bottle as sample system.

32. Measuring system according to claim 31, wherein the measuring adapter is formed as a stopper for a sample bottle which is present as sample system and which stopper can be inserted in particular into a bottle neck of the sample bottle.

33. Measuring system according to claim 30 wherein the measuring adapter has a flanged connection.

34. Measuring system according to claim 30 wherein the measuring adapter has a screw thread.

35. Measuring system according to claim 30 wherein the measuring adapter has a snap-on device.

36. Measuring system according to claim 30 wherein the measuring adapter contains a diffusion pipe as diffusion seal.

37. Measuring system according to claim 30 wherein the measuring adapter contains at least one opening as diffusion seal.

38. Measuring system according to claim 30 wherein the measuring adapter contains a cannula as diffusion seal.

39. Measuring system according to claim 38, wherein the sample system is sealed with an elastomer seal and the measuring adapter contains a cannula for penetrating the seal as diffusion seal.

* * * * *

UNITED STATES PATENT AND TRADEMARK OFFICE
CERTIFICATE OF CORRECTION

PATENT NO. : 6,903,823 B1
DATED : June 7, 2005
INVENTOR(S) : Holger Müller et al.

It is certified that error appears in the above-identified patent and that said Letters Patent is hereby corrected as shown below:

<u>Title page,</u>
Item [76], Inventor, the second inventor's name "Udo Schmala" should read -- Udo Schmale --.

Signed and Sealed this

Thirteenth Day of September, 2005

JON W. DUDAS
*Director of the United States Patent and Trademark Office*